United States Patent [19]

Dorn

[11] Patent Number: 4,542,158

[45] Date of Patent: Sep. 17, 1985

[54] PRODRUG ESTERS OF DIFLUNISAL AND RELATED COMPOUNDS

[75] Inventor: Conrad P. Dorn, Plainfield, N.J.

[73] Assignee: Merck & Co., Inc., Rahway, N.J.

[21] Appl. No.: 435,151

[22] Filed: Oct. 25, 1982

Related U.S. Application Data

[63] Continuation-in-part of Ser. No. 332,426, Dec. 21, 1981, abandoned.

[51] Int. Cl.[4] .................. A61K 31/265; C07C 69/96
[52] U.S. Cl. ................................. 514/512; 260/463
[58] Field of Search ..................... 260/463; 424/301

[56] References Cited

U.S. PATENT DOCUMENTS 3,590,082  6/1971  Sarett et al. ..................... 260/463
3,714,226  1/1973  Ruyle et al. ..................... 424/250
4,417,064  11/1983  Mehta ............................. 260/463
4,426,391  1/1984  Alexander et al. ............. 424/301

OTHER PUBLICATIONS

N. O. Bodin, et al., *Antimicrobial Agents and Chemotherapy*, vol. 8, No. 5, pp. 518–525, (1975).

*Primary Examiner*—Diana G. Rivers
*Attorney, Agent, or Firm*—Theresa Y. Cheng; Mario A. Monaco

[57]  ABSTRACT

1-(Alkoxy or aroxy)carbonyloxyalkyl esters of diflunisal and related compounds are stable in aqueous medium and non-irritant to mucous membranes of mouth, throat, and stomach. Accordingly, they are useful Prodrugs of the analgesic and anti-inflammatory drug, diflunisal.

6 Claims, No Drawings

PRODRUG ESTERS OF DIFLUNISAL AND RELATED COMPOUNDS

RELATED APPLICATION

This application is a continuation-in-part of application Ser. No. 332,426, filed Dec. 21, 1981, now abandoned.

BACKGROUND OF THE INVENTION

The present invention relates to novel and stable 1-(alkoxy or aroxy)carbonyl esters of diflunisal, i.e., 2-hydroxy-5-(2,4-difluorophenyl)benzoic acid and related compounds characterized as being:

(1) readily bioavailable;
(2) stable in aqueous formulation;
(3) non-irritant to mucous membranes of mouth, throat, and stomach when administered, and
(4) having long duration.

Diflunisal and its analogs are known analgesic and anti-inflammatory agents of high potency, long duration but low gastric irritation. It is disclosed in U.S. Pat. No. 3,714,226 issued Jan. 30, 1973 to William V. Ruyle et al. However, it has been found that because of its inherent property as a phenolic free acid, diflunisal is irritant to mucous membranes and is therefore unsuitable for oral aqueous or suppository formulations. Particularly, in long term chronic dosing, the irritancy of diflunisal especially its aqueous suspension may have undesirable effects on the histology of the mucous membranes, e.g., mucosa of mouth and throat. On the other hand, aqueous suspensions of the novel esters of this invention are devoid of the irritancy and can be administered to infants, the very old, or chronic patients having difficulty in swallowing tablets, capsules or other forms of oral dose. Furthermore, it should be noted that the novel esters of this invention are stable in vitro at physiological pH ranges (1.2–8) but are readily cleaved during absorption by the mucous membranes. The products of cleavage from the ester, i.e., carbon dioxide, acetaldehyde and alcohols are advantageously physiologic in nature.

Another aspect of the present invention involves the improved solubility range of the novel alkoxycarbonyl-alkyl esters which are slightly less soluble in water but more soluble in organic solvents, e.g., 1,3-butenediol, mono- or diglycerides, than diflunisal. This improved solubility facilitates the preparation of aqueous or oleaginous formulations for parenteral injections.

Accordingly, it is an object of the present invention to provide novel and stable 1-(alkoxy or aroxy)carbonyloxyalkyl esters of diflunisal and related compounds particularly suitable for aqueous oral or suppository formulations.

Another object of the present invention is to provide processes for the preparation of these novel esters.

Still another object of the present invention is to provide a pharmaceutical composition particularly suitable for parenteral, oral and/or, suppository formulation comprising a pharmaceutically acceptable carrier and an effective amount of the novel esters for the treatment of pain, fever and inflammation.

Finally, it is the ultimate object of the present invention to provide a method of treating inflammation, pain and fever comprising the administration of an effective amount of the novel esters or a pharmaceutical composition thereof to a mammal in need of such treatment.

DETAILED DESCRIPTION OF THE INVENTION

This invention relates to 1-(alkoxy or aroxy)carbonyloxyalkyl esters of diflunisal and related compounds having the structural formula (I):

[Structural formula I showing biphenyl with $X_{(1-5)}$ substituents, $OR^2$, $R^3$, and $C(=O)-OCH(R^1)-OC(=O)-OR$ group]

wherein
R is
(a) lower alkyl especially $C_{1-6}$ alkyl such as methyl, ethyl, i-propyl, t-butyl or hexyl;
(b) lower cycloalkyl especially $C_{3-8}$ cycloalkyl, e.g., cyclopropyl, cyclopentyl or cyclohexyl;
(c) unsubstituted or substituted aryl for example, phenyl, 4-methoxyphenyl, 4-methylthiophenyl, 2,4-dimethylphenyl, 3-chlorophenyl, 4-ethylthiophenyl, 4-methylsulfinylphenyl or 4-methylsulfonylphenyl; and
(d) aralkyl especially aryl $C_{1-6}$alkyl such as benzyl, 4-methoxybenzyl, or benzhydryl;

$R^1$ is
(a) hydrogen;
(b) lower alkyl;
(c) lower cycloalkyl; or
(d) aryl $R^2$ is
(a) hydrogen;
(b) lower alkanoyl especially $C_{1-6}$alkanoyl such as acetyl, propionyl and butyryl; or
(c) lower alkoxycarbonyl such as ethoxycarbonyl or butoxycarbonyl;

$R^3$ is
(a) hydrogen; or
(b) lower alkyl; and

X is halo especially chloro or fluoro, X being on one or more of the phenyl carbons.

In the preferred aspects of this invention,
R is lower alkyl or unsubstituted or substituted aryl;
$R^1$ is hydrogen or lower alkyl;
$R^2$ is hydrogen; and
X is fluoro; X being on the 2- and/or 4-position of the benzene ring.

In the more preferred aspects of this invention, the compounds are the 1-(alkoxy or aroxy)carbonyloxyalkyl esters of diflunisal of the formula:

[Structural formula showing difluorobiphenyl with OH and $C(=O)-O-CH(R^1)-O-C(=O)-OR$ group]

wherein
R is loweralkyl especially $C_{1-6}$alkyl or aryl; and
$R^1$ is hydrogen or $C_{1-6}$alkyl.

In the most preferred embodiment of this invention, the compound is of the formula:

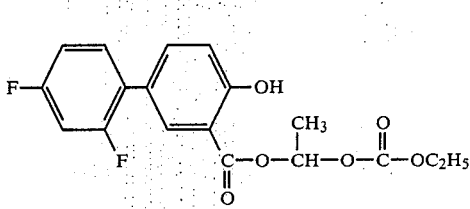

The novel esters of the present invention are prepared by a process comprising the treatment of a compound of structural formula:

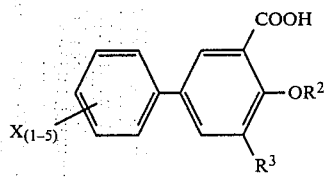

with a base and an α-halo carbonate of formula (II):

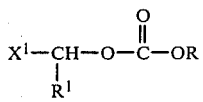

wherein $X^1$ is halo especially chloro or bromo with or without a solvent.

The base used in the esterification may be a hydroxide, a carbonate or a bicarbonate of $Na^+$, $K^+$, $Li^+$, $Ca^{++}$, $Ag^+$, $Cu^+$ or $Hg^{++}$; tetralkylammonium hydroxide, i.e., (loweralkyl)$_4^+$OH$^-$, such as tetramethyl ammonium hydroxide and tetra(n-butyl)ammonium hydroxide; trialkylamine, i.e., (loweralkyl)$_3$NH, such as triethylamine, tripropylamine and tri(t-butyl)amine; or sodium hydride. Although solvent is not necessary to the esterification, it is preferable that a solution of diflunisal or its derivative in an organic solvent such as benzene or substituted benzene including toluene, xylene, chlorobenzene, ethylbenzene, methoxybenzene, p-methoxytoluene, or the like, dimethylformamide (DMF), chloroform, methylchloroform, methylene chloride, ethylacetate, a dialkyl ether including diethylether, tetrahydrofuran, or a mixture thereof, is treated with a base such as triethylamine, sodium hydride or sodium hydroxide to form the corresponding salt of diflunisal or its derivative. Subsequently, an α-halocarbonate such as ethyl 1-chloroethyl carbonate i.e. 1-chloro-diethyl carbonate is added and the resulting mixture is stirred at from about 0° C. to about 150° C., preferably at about 25° C. to about 120° C. until the esterification is substantially complete.

The α-halocarbonates of formula (II) are either available commercially or can be prepared from known compounds via conventional methods.

Alternatively, the novel esters of the present invention are prepared by a process whereby a 1-(alkoxy or aroxy)carbonyloxyalkyl ester of salicylic acid is prepared according to the esterification procedures described above followed by direct coupling with a halogenated benzene:

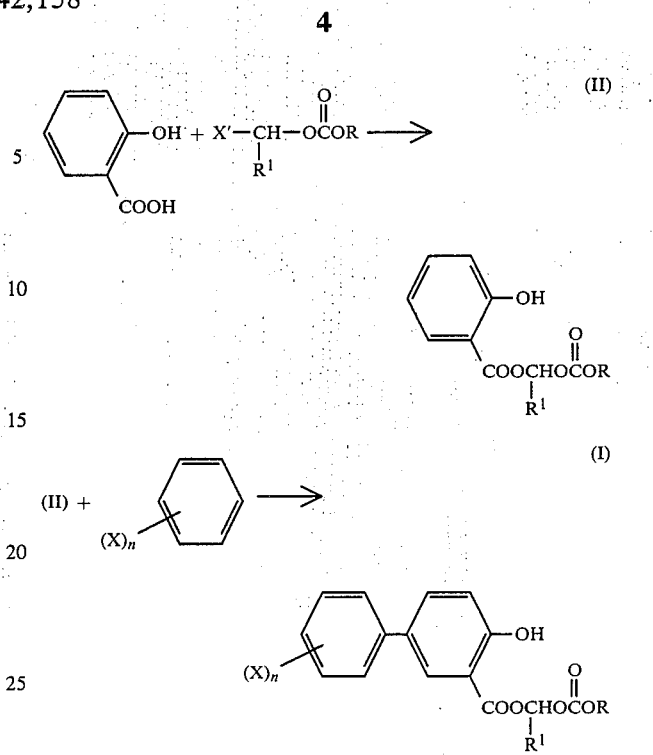

The coupling reaction is usually conducted under an oxygen atmosphere (from atmospheric to about 750 psig) in the presence of a palladium catalyst such as palladium acetate or palladium chloride. A preferred procedure of coupling involves a palladium catalyst system which comprises:

A. A catalyst portion comprising:
(1) palladium together with
(2) $C_{1-2}$COO— ligands and halo ligands selected from the group consisting of bromo, chloro and fluoro, such that the molar weight percent, based on total ligand molar weight, of the the $C_{1-2}$COO— ligands is from 30 to 60%; wherein the $C_{1-2}$COO— ligands are provided as palladium or alkali metal, acetate or propionate, and said halo ligands are provided as the appropriate halo salt of palladium, lithium, sodium, or tetra(alkyl)ammonium; wherein the ratio of the total molar weight amount of the ligands to the molar weight amount of palladium utilized is from 4:1 to 10:1; and
(3) from 10 to 100 parts of a reaction promoting acid, per part, on a molar basis of palladium catalyst; and B. a catalyst regeneration portion comprising:
(1) from 0.1 to 8.0 parts of phosphomolybdenovanadic acid per part, on a molar basis, of palladium catalyst; and
(2) at least 20 parts of a solubilizing agent selected from the group consisting of ethylene carbonate, propylene carbonate, and sulfolane, per part, on a molar basis, of palladium catalyst.

This coupling method is described in detail in U.S. Pat. No. 4,237,315 issued to Ulf H. Dolling on Dec. 2, 1980, and is herein incorporated by reference.

Furthermore, the novel esters of the present invention wherein $R^1$ is methyl can be prepared by a process involving the formation of a vinyl ester (III) followed by hydrochlorination and treatment with a compound of structural formula:

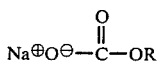

wherein R is as previously defined to form the esters of formula (I):

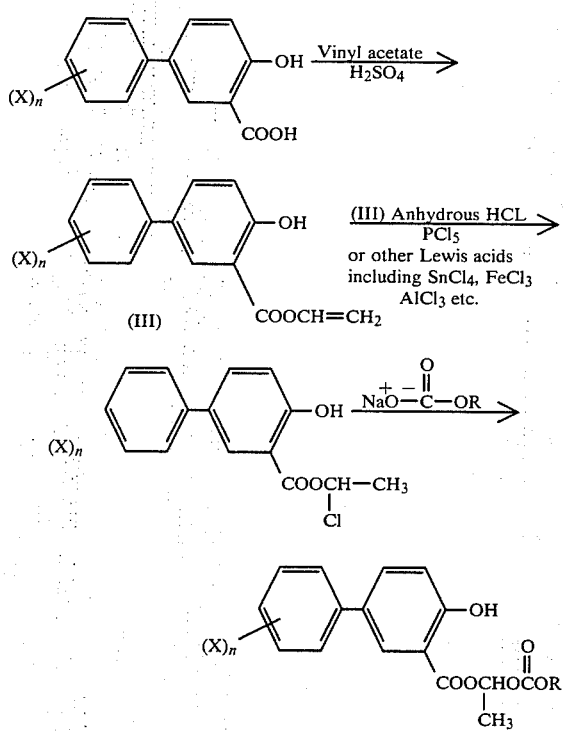

This invention also relates to a method of treating inflammation comprising the administration of a compound of Formula (I) as the active constituent.

It has been found that the compounds of Formula (I) possess anti-inflammatory, antipyretic and analgesic activities. More specifically the compounds of the present invention are prodrugs of diflunisal and related compounds useful for reducing inflammation and relieving pain in a variety of diseases, e.g., rheumatoid arthritis, osteoarthritis, gout, infectious arthritis and rheumatic fever. At similar dosages as prescribed for the parent compounds, they may be administered by conventional methods to a patient suffering from inflammation, pain and fever. It has been established that compounds of Formula (I) are readily hydrolyzed in vivo by enzymes and/or gut fluora to release tne parent compounds, e.g., diflunisal. Other products from the hydrolysis, for example, those from 1-(ethoxycarbonyloxy)ethyl 5-(2,4-difluorophenyl) salicylate, are carbon dioxide, acetaldehyde or alcohol, all of which are easily disposed of physiologically by the body and therefore present no problems of toxicity or adverse side effects.

Accordingly, for treatment of inflammation, the compounds of this invention may be administered orally, parenterally, topically or rectally to a patient in need of such treatment in dosage unit formulations containing a non-toxic pharmaceutically acceptable carrier. The term parenteral as used above includes subcutaneous, intramuscular or intrasternal injection or infusion techniques.

Preferably, the compounds of this invention are administered orally in aqueous, tablet or suppository formulations. The term aqueous formulation includes all pharmaceutical compositions or formulations which contain water. Parenteral administrations with aqueous or oleaginous suspensions are also the preferred method of treatment of this invention.

The pharmaceutical compositions containing the active ingredient may be in a form suitable for oral use, for example, as tablets, troches, lozenges, aqueous or oily suspensions preferably in aqueous suspensions; dispersible powders; dry or wet granules; emulsions; hard or soft capsules; syrups; or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation.

Tablets usually contain the active ingredient in admixture with non-toxic pharmaceutically acceptable excipients which are suitable for the manufacture of tablets. These excipients may be for example, inert diluents such as calcium carbonate, sodium carbonate, lactose, calcium phosphate or sodium phosphate; granulating and disintegrating agents, for example, maize starch, or alginic acid; binding agents, for example starch, gelatine or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatine capsules wherein the active ingredient is mixed with an inert solid diluent, for example, calcium carbonate, calcium phosphate or kaolin, or as soft gelatine capsules wherein the active ingredient is mixed with water or an oil medium, for example peanut oil, liquid paraffin, or olive oil.

The preferred oral aqueous suspensions of this invention generally contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidine, gum tragacanth and gum acacia; dispersing or wetting agents which may be a naturally-occurring phosphatide, for example lecithin; condensation products of an alkylene oxide with fatty acids, for example polyoxyethylene stearate; condensation products of ethylene oxide with long chain aliphatic alcohols, for example heptadecaethyleneoxycetanol; condensation products of ethylene oxide with partial esters derived from fatty acids and a hexitol such as polyoxyethylene sorbitol monooleate; or condensation products of ethylene oxide with partial esters derived from fatty acids and hexitol anhydrides, for example polyoxyethylene sorbitan monooleate. The said aqueous suspensions may also contain one or more preservatives, for example, ethyl- or n-propyl- p-hydroxybenzoate, one or more coloring agents, one or more flavoring agents, and one or more sweetening agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such a those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting and suspending agents are exemplified by those already mentioned above. Additional excipients, for example, sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurrng phosphatides, for example soya bean lecithin, and esters or partial esters derived from fatty acids and hexitol anhydrides, for example sorbitan mono-oleate, and condensation products of the said partial esters with ethylene oxide, for example polyoxyethylene sorbitan mono-oleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents.

The pharmaceutical compositions may be in the form of a sterile injectable preparation, for example as a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol or other suitable nontoxic organic solvent. Among the acceptable vehicles that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Preferably, the compounds of this invention may be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols. For example, a molten solution of the diflunisal ester and polyethylene glycol is prepared, to which is added glycerol. This product may be prepared at those temperatures which will provide a molten state. The mass is then sub-divided into suppository doses and allowed to congeal by lowering the temperature of the system. It is preferred to congeal at room temperature.

The polyethylene glycol base may be made from any suitable pharmaceutical grade polyethylene glycol or mixtures thereof of various molecular weights which are used to prepare suppositories that are soluble in water and in the secretions of mucous membranes. Representative polyethylene glycol bases are polyethylene glycol 1000, 1540, 4000 and 6000. The selection of the exact composition of the base will, of course, depend on the properties desired in the suppository, such as solubility, congealing temperature, size, etc. The more preferred bases are those prepared from polyethylene glycol 4000 and polyethylene glycol 6000. The amount of the base employed in this invention is not critical and will depend on the overall size of the suppository, the desired use, and the dosage of diflunisal in each suppository. For example, the amount of base can vary from about 50% to 95% by weight of the suppository.

For topical use, creams, ointments, jellies, solutions, or suspensions, etc., containing the anti-inflammatory agents are employed.

Dosage levels of the order from 0.2 mg to 140 mg per kilogram of body weight per day are useful in the treatment of the above-indicated conditions (10 mg to 7 gms per patient per day). For example, inflammation is effectively treated and anti-pyretic and analygesic activity manifested by the administration from about 0.5 to 50 mg of the compound per kilogram of body weight per day (25 mg to 3.5 gms per patient per day). Advantageously, from about 2 mg to about 20 mg per kilogram of body weight per daily dosage produces highly effective results (100 mg to 2 gm per patient per day).

The amount of active ingredient that may be combined with the carrier materials to produce a single dosage form will vary depending upon the host treated and the particular mode of administration. For example, a formulation intended for the oral administration of humans may contain from 5 mg to 5 gm of active agent compounded with an appropriate and convenient amount of carrier material which may vary from about 5 to about 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

EXAMPLE 1

1-(Ethoxycarbonyloxy)ethyl
5-(2,4-difluorophenyl)salicylate

To a solution of diflunisal (5.0 g) in 40 ml DMF was added 0.8 g of sodium hydride (oil suspension containing 60% of NaH). The resultant mixture was stirred for 1.5 hours at room temperature before 3.0 ml of ethyl 1-chloroethyl carbonate was added dropwise. The reaction mixture was stirred at room temperature overnight and concentrated in vacuo. The concentrate was partitioned between ether/ethyl acetate and acidified water. The organic layer was separated and the aqueous layer was extracted again with ether. The organic layers were combined, washed well with water, dried over anhydrous sodium sulfate and concentrated to 6.6 g of crude product. After further purification by chromatography (eluted through 120 g of silica gel with hexane, and then 5% ethyl acetate in hexane), the product was crystallized from hexane to afford 3.71 g of 1-(ethoxycarbonyloxy)ethyl 5-(2,4-difluorophenyl)salicylate. m.p. 63.5°–65.0° C. (lower melting form I).

Anal. Calcd. for $C_{18}H_{16}F_2O_6$: C, 59.02; H, 4.40. Found: C, 59.11; H, 4.34.

EXAMPLE 2

1-(Ethoxycarbonyloxy)ethyl 5-(2,4-difluorophenyl)salicylate

Diflunisal (2.5 g) was dissolved in 30 ml of chloroform containing 1.1 g triethylamine. While stirring at room temperature, ethyl 1-chloroethylcarbonate (1.66 g) was added slowly and the resulting reaction mixture was heated and refluxed for about 67 hours. After cooling, the mixture was concentrated in vacuo. The concentrate was partitioned twice between ether (200 ml) and water, and the organic extracts combined. After chromatography and crystallization as described in Example 1, there was afforded 38.5 g of crystalline product (crystallized from 5% ethylacetate in hexane), m.p. 79°–80.5° C. (higher melting form II).

EXAMPLE 3

1-(Ethoxycarbonyloxy)ethyl 5-(2,4-difluorophenyl)salicylate

A suspension of diflunisal (12.51 g) in 40 ml of methylchloroform was stirred at room temperature while 5.2 g triethylamine and 9.0 g of ethyl 1-chloroethylcarbonate were added sequentially. The resultant solution was heated and refluxed for 90 hours before it was cooled and then poured into 50 ml of diluted aqueous hydrochloric acid (5 ml of concentrated HCl in 45 ml of water). The mixture was stirred vigorously and precipitation occured. The resultant precipitate was filtered, washed with 20 ml methylchloroform-hexane (1:1) to afford 1.65 g of unreacted diflunisal. The filtrates were combined and the organic layer separated. It was washed with water (100 ml), dried over anhydrous sodium sulfate and concentrated in vacuo. Crystallization occured upon seeding and 14.60 g (91.8%) of purified 1-(ethyoxycarbonyloxy)ethyl 5-(2,4-difluorophenyl)-salicylate was obtained. M.p. 78°–79.5° C.

Following substantially the same procedure as described above, but substituting for ethyl 1-chloroethylethylcarbonate used therein the following chlorocarbonates as shown in Table I, there are obtained the corresponding 1-(alkoxy or aroxy) carbonyloxyalkyl esters of diflunisal also shown in Table I.

TABLE I

Diflunisal + X—CHOCOR —→
           |         ||
           R¹         O

| X | R¹ | R |
|---|-----|-----|
| Cl | $C_2H_5$ | $C_2H_5$ |

TABLE I-continued

Diflunisal + X—CHOCOR —→
           |         ||
           R¹         O

| X | R¹ | R |
|---|-----|-----|
| Cl | $CH_3$ | $CH_2C_6H_5$ |
| Br | $n$-$C_3H_7$ | $t$-$C_4H_9$ |
| Br | $CH_3$ | $CH(C_6H_5)_2$ |
| Cl | $C_6H_5$ | $CH_3$ |
| Br | cyclo$C_6H_{11}$ | $p$-$CH_3O$—$C_6H_5$ |

EXAMPLE 4

1-(Ethoxycarbonyloxy)ethyl 5-(2,4-difluorophenyl)salicylate

Triethylamine (885 mg) was added to a stirred slurry of 5-(2,4-difluorophenyl)salicylic acid in toluene (6.5 ml) under nitrogen. The resulting mixture was stirred for about 2 hours before ethyl 1-chloroethylcarbonate (1.53 g) was added, and the resulting solution heated at reflux until reaction was complete.

The reaction mixture was cooled and then added to aqueous hydrochloric acid solution. After thorough mixing, the layers were separated and the organic layers washed with water, dried and filtered. The solvent was removed under reduced pressure, leaving a pale oil which was crystallized from aqueous methanol to afford 2.84 g (91%) of 1-(ethoxycarbonyloxy) 5-(2,4-difluorophenyl)salicylate, m.p. 79°–80° C.

EXAMPLE 5

1-(Ethoxycarbonyloxy)ethyl 5-(2,4-difluorophenyl)salicylate

A mixture of 1.76 g of the triethylamine salt of diflunisal and 1.0 g of 1-chloroethyl ethyl carbonate are heated in an oil bath at 100°–110° with magnetic stirring for 3 hours. The reaction mixture is then cooled to room temperature and 5 ml of methanol are added. After cooling to 0°–5°, the resulting precipitate is collected by filtration, washed with 3 ml of cold methanol then with 5 ml of 10% ethyl ether in hexane. After air drying there is obtained 1.38 g ( 75%) of 1-(ethoxycarbonyloxy)ethyl 5-(2,4-difluorophenyl)salicylate, m.p. 76°–78°.

EXAMPLE 6

1-(Ethoxycarbonyloxy)ethyl 5-(2,4-difluorophenyl)salicylate

Step A: Preparation of 1-(ethoxycarbonyloxy)ethylsalicylate

A mixture of 2.76 g salicylic acid, 2.02 g triethylamine and 3.5 gm 1-chloroethyl ethyl carbonate in 25 ml of toluene is refluxed for three hours. The reaction mixture is cooled and 25 ml of ether and 25 ml of water added. The organic layer is separated, washed 2× with 25 ml water, dried through sodium sulfate and concentrated in vacuo. The residue (3.88 g) is chromatographed on 200 g silica gel. Elution with 25% methylene chloride in hexane gives 1-(ethoxycarbonyloxy)ethyl salicylate which is directly used in the next step.

Step B: Preparation of 1-(ethoxycarbonyloxy)ethyl 5-(2,4-difluorophenyl)salicylate A glass-lined autoclave is charged with 1 mmole of palladium acetate, 5 mmole of sodium chloride, 1.6 mmole of sodium acetate, 2 mmole of phosphomolybdenovanadic acid, 10 g of ethylene carbonate, 5.0 ml of acetic acid, 465 mmole of 1-(ethoxycarbonyloxy)ethyl salicylate, and 510 mmole of m-difluorobenzene. The mixture is stirred for 48 hours at 90° C. and under 200 psi oxygen pressure. The solution is cooled to 25° C. and excess m-difluorobenzene is removed by distillation. Fifty ml of water and 150 ml of toluene are then added to the residue. The pH is adjusted to 7–8 with aqueous sodium hydroxide (80 mmoles). The layers are separated and the aqueous solution is extracted with 150 ml of toluene. The toluene and then the excess starting materials are removed by distillation. The resulting residue is recrystallized from methanol to obtain pure 1-(ethoxycarbonyloxy)ethyl 5-(2,4-difluorophenyl)salicylate.

EXAMPLE 7

1-(Ethoxycarbonyloxy)ethyl 5-(2,4-fluorophenyl)salicylate

Step A: Preparation of vinyl 5-(2,4-difluorophenyl)salicylate 5-(2,4-Difluorophenyl)salicylic acid (1 mol), an excess amount of vinyl acetate (10 mole) and catalytic amounts of Hg(OAc)$_2$ ( 6 g) and conc. H$_2$SO$_4$ ( 0.1 ml) are mixed at room temperature for 5 days. Excess 5-(2,4-difluorophenyl)salicylic acid is removed and sodium acetate is added to neutralize the reaction. Excess vinyl acetate is removed to obtain the product, vinyl 5-(2,4-difluorophenyl) salicylate.

Step B: Preparation of 1-chloroethyl 5-(2,4-difluorophenyl)salicylate

To a mixture of vinyl 5-(2,4-difluorophenyl)salicylate (15 g) and 0.1 g dry PCl$_5$, HCl gas is passed for about one hour at about 120°–125° C. Upon cooling, the crude product crystallizes and is collected by filtration. Recrystallization from methanol yields pure 1-chloroethyl 5-(2,4-difluorophenyl)salicylate.

Step C: Preparation of 1-(ethoxycarbonyloxy)ethyl 5-(2,4-difluorophenyl)salicylate To a solution of 1-chloroethyl 5-(2,4-difluorophenyl)salicylate (5.0 g) in about 40 ml of DMF is added portionwise 3.0 g of sodium ethyl carbonate. The reaction is stirred at room temperature and then concentrated in vacuo. The concentrate is partitioned between ether/ethyl acetate and acidified water. The organic layer is separated and the aqueous layer is again extracted with ether, the organic layers are pooled and washed with water followed by drying and concentration to the crude product. After further purification by chromatography as described in Example 1, the product is crystallized from hexane to afford pure 1-(ethoxycarbonyloxy)ethyl 5-(2,4-difluorophenyl)salicylate.

EXAMPLE 8

Oral Suspension of 1-(ethoxycarbonyloxy)ethyl 5-(2,4-difluorophenyl)salicylate

| Component | mg/ml |
| --- | --- |
| 1-(ethoxycarbonyloxy) ethyl 5-(2,4-difluorophenyl) salicylate | 366.25 |
| AVICEL Microcrystalline Cellulose NF Sodium Carboxymethylcellulose USP | 50.00 |
| Methylcellulose USP | 25.00 |
| Sorbic Acid NF | 5.00 |
| Docusate Sodium USP | 0.50 |
| Purified Water USP | 2.50 |
| Antifoam Emulsion q.s. | |
| Sorbitol Solution 70% w/v to 5.0 ml | |

The docusate sodium was dissolved in a small volume of water and added to the bulk in a suitable vessel. The Avicel was dispersed with agitation and allowed to hydrate. The remaining materials were then added with agitation and the suspension made to volume with Sorbitol Solution. The completed suspension was homogenized.

What is claimed is:

1. A compound of structural formula (I):

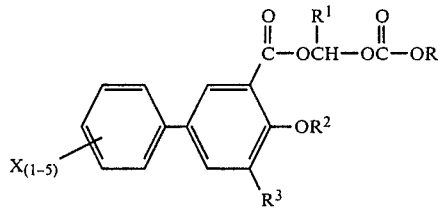

wherein:
R is
   (a) C$_{1-6}$alkyl; or
   (b) C$_{3-6}$cycloalkyl;
R$^1$ is
   (a) hydrogen;
   (b) C$_{1-6}$alkyl; or
   (c) C$_{3-6}$cycloalkyl;
R$^2$ is
   (a) hydrogen;
   (b) C$_{1-6}$alkanoyl;
   (c) C$_{1-6}$alkoxycarbonyl;
R$^3$ is
   (a) hydrogen; or
   (b) C$_{1-6}$alkyl; and
X is halo.

2. The compound of claim 1 having the structural formula:

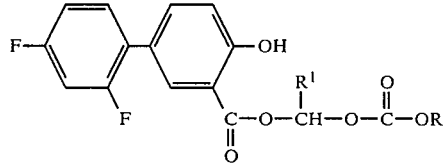

wherein
R is
   (a) C$_{1-6}$alkyl; and

R[1] is
    hydrogen or $C_{1-6}$alkyl.

3. The compound of claim 1 having the structural formula:

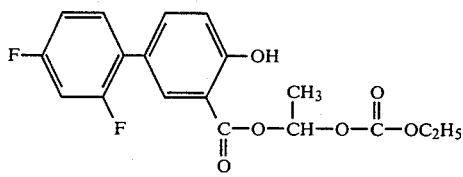

4. A pharmaceutical composition for treating and/or controlling inflammation, pain or fever in a mammal comprising a pharmaceutical carrier and an effective amount of a compound of formula:

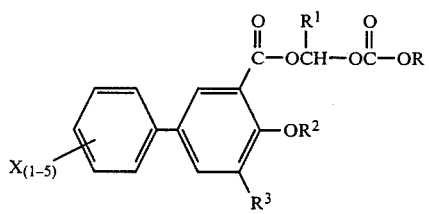
(I)

wherein:
R is
    (a) $C_{1-6}$alkyl; or
    (b) $C_{3-6}$cycloalkyl;
R[1] is
    (a) hydrogen;
    (b) $C_{1-6}$alkyl; or
    (c) $C_{3-6}$cylcoalkyl;
R[2] is
    (a) hydrogen;
    (b) $C_{1-6}$alkanoyl;
    (c) $C_{1-6}$alkoxycarbonyl;
R[3] is
    (a) hydrogen; or
    (b) $C_{1-6}$alkyl; and
X is halo.

5. A method of treating and/or controlling inflammation, pain and fever comprising the administration of a mammal in need of such treatment an effective amount of a compound of formula:

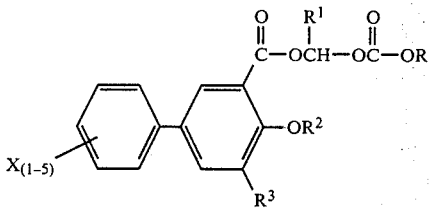

wherein:
R is
    (a) $C_{1-6}$alkyl; or
    (b) $C_{3-6}$cycloalkyl;
R[1] is
    (a) hydrogen;
    (b) $C_{1-6}$alkyl; or
    (c) $C_{3-6}$cycloalkyl;
R[2] is
    (a) hydrogen;
    (b) $C_{1-6}$alkanoyl;
    (c) $C_{1-6}$alkoxycarbonyl;
R[3] is
    (a) hydrogen; or
    (b) $C_{1-6}$alkyl; and
X is halo.

6. The method of claim 5 wherein the compound is of structural formula:

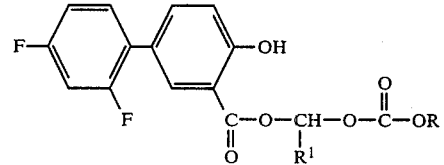

wherein
    R is $C_{1-6}$alkyl; and
    R[1] is hydrogen or $C_{1-6}$alkyl.

* * * * *